US012502516B2

(12) United States Patent
Nalawade et al.

(10) Patent No.: US 12,502,516 B2
(45) Date of Patent: Dec. 23, 2025

(54) DISINFECTION DEVICE FOR FEMALE CONNECTORS

(71) Applicant: Becton, Dickinson and Company, Franklin Lakes, NJ (US)

(72) Inventors: Praveen Nalawade, Belgaum (IN); Amit Kumar, Bengaluru (IN); Narsi Reddy Sanikommu, Prakasam District (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 575 days.

(21) Appl. No.: 18/071,756

(22) Filed: Nov. 30, 2022

(65) Prior Publication Data

US 2024/0173537 A1 May 30, 2024

(51) Int. Cl.
*A61M 39/16* (2006.01)

(52) U.S. Cl.
CPC ........ *A61M 39/162* (2013.01); *A61M 39/165* (2013.01); *A61M 2205/584* (2013.01)

(58) Field of Classification Search
CPC .. A61M 39/16; A61M 39/162; A61M 39/165; A61M 39/20; A61L 2202/123; A61L 2202/24; A61L 2/26
See application file for complete search history.

(56) References Cited

U.S. PATENT DOCUMENTS 7,241,275 B2 * 7/2007 Alchas ................ A61M 5/3202 604/117
7,931,877 B2 4/2011 Steffens et al.
9,192,449 B2 11/2015 Kerr et al.
12,067,438 B2 * 8/2024 Leibbrand ............. A61M 39/20
2018/0256883 A1 9/2018 Follman et al.
2020/0197686 A1 6/2020 Anderson et al.
2020/0276346 A1 9/2020 Drmanovic
2021/0322750 A1 10/2021 Harandi et al.
2023/0226338 A1 * 7/2023 Albertsen .......... A61M 39/1011 604/93.01
2024/0173538 A1 * 5/2024 Nalawade ................. A61L 2/18
2024/0198076 A1 * 6/2024 Fernandez ............ A61M 39/16

OTHER PUBLICATIONS

"PCT International Search Report and Written Opinion in PCT/US2023/081546 dated Apr. 5, 2024, 12 pages".

* cited by examiner

*Primary Examiner* — Nathan R Price
(74) *Attorney, Agent, or Firm* — Servilla Whitney LLC

(57) ABSTRACT

A disinfection device for disinfecting a female medical connector. The device includes an inner housing having an absorbent material that includes a disinfectant or antimicrobial agent that receives the connector. The device also includes an outer housing having an outer wall that receives the inner housing wherein the inner housing is rotatable within the outer housing. An indicator is located between the outer wall and a transparent collar that includes at least one rib. The indicator includes a first visual indicator and a second visual indicator concealed by the first visual indicator. The inner housing includes a boss element that extends through the outer wall and indicator and is attached to the collar. Rotation of the collar causes rotation of the absorbent material and causes the rib to remove sufficient portions of the indicator to expose the second visual indicator to provide visual indication that the connector is disinfected.

20 Claims, 7 Drawing Sheets

DISINFECTION DEVICE FOR FEMALE CONNECTORS

TECHNICAL FIELD

The present disclosure generally relates to a device for disinfecting and sterilizing female medical connectors, and more particularly, to a disinfection device including an indicator element and a transparent collar having at least one rib wherein rotation of the collar causes the at least one rib to remove sufficient portions of the indicator element to expose a visual indicator to provide visual indication that the female connector is disinfected.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs, ports or valves upon connection to the VAD when delivering a fluid or pharmaceutical. Each access hub, port, valve or connection is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and caps are also incorporated into the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable. In particular, it has been found that health care providers may not completely understand the impact of not following scrubbing protocols. As a result, a health care provider may not disinfect the hub for the recommended amount of time.

Thus, there is a need for a disinfection cap that enables disinfection of the needleless connector while also enhancing compliance to the clinical practice of "scrubbing-the-hub" before accessing the line.

SUMMARY

An aspect of the present disclosure pertains to a disinfection device for disinfecting a female medical connector. According to an exemplary embodiment of the present disclosure, the device generally comprises an absorbent material having a disinfectant or antimicrobial agent, inner and outer housings, an indicator element, a transparent collar and a boss element. The inner housing includes an inner wall and a first open end that receives the absorbent material wherein the female connector is inserted into the first open end and contacts the absorbent material. The outer housing includes an outer wall and a second open end that receives the inner housing wherein the inner housing and absorbent material are rotatable within the outer housing. The indicator element is located between the outer wall and the transparent collar wherein the indicator element includes a first visual indicator and a second visual indicator concealed by the first visual indicator. In addition, the collar includes at least one rib element that contacts the indicator element. The boss element extends from the inner wall and through the outer wall and indicator element and is attached to the collar. Rotation of the collar causes corresponding rotation of the absorbent material to disinfect the female connector. Rotation of the collar also causes the at least one rib element to remove sufficient portions of the indicator element to expose the second visual indicator to provide visual indication that the female connector is disinfected.

In one or more embodiments, the female medical connector is selected from a group consisting of needleless connectors, catheter luer connectors, stopcocks, or hemodialysis connectors.

In an embodiment, the female medical connector is a needleless connector having an access surface, septum, hub surface and hub threads.

In one or more embodiments, the indicator element is a scratch card having a removable scratch card surface.

In an embodiment, the indicator element includes an indicator surface fabricated using a layer of removable foil.

In one or more embodiments, the first visual indicator is a first color and the second visual indicator is a second color.

The outer housing may also include a plurality of flanges that extend from the outer housing to facilitate handling of the outer housing by a user.

In an embodiment, the collar includes a plurality of raised grip members to facilitate gripping the collar by a user.

In another exemplary embodiment of the present disclosure, the device generally comprises an absorbent material having a disinfectant or antimicrobial agent inner and outer housings, an indicator element, a transparent collar, a boss element and a ring member attached to the outer housing and coupled to the collar. The inner housing includes an inner wall and a first open end that receives the absorbent material wherein the female connector is inserted into the first open end and contacts the absorbent material. The outer housing includes an outer wall and a second open end that receives the inner housing wherein the inner housing and absorbent material are rotatable within the outer housing. The outer housing further includes a plurality of flanges that extend from the outer housing to facilitate handling of the outer housing by a user. The indicator element is located between the outer wall and the transparent collar wherein the indicator element includes a first visual indicator and a second visual indicator concealed by the first visual indicator. In addition, the collar includes at least one rib element that contacts the indicator element. The boss element extends from the inner wall and through the outer wall and indicator element and is attached to the collar. Rotation of the collar causes corresponding rotation of the absorbent material to disinfect the female connector. Rotation of the collar also causes the at least one rib element to remove sufficient portions of the indicator element to expose the second visual indicator to provide visual indication that the female connector is disinfected. The ring member is coupled to the collar by a plurality of breakable elements to form a tamper evident structure wherein the breakable elements are configured to break when the collar is rotated with sufficient torque wherein broken finger elements indicate that the collar has been rotated.

In an embodiment, the second open end forms an annular engagement surface and the disinfection device further includes a peelable seal removably attached to the annular engagement surface to prevent the disinfectant or the antimicrobial agent from exiting the disinfection device.

In one or more embodiments, the disinfectant or antimicrobial agent is selected from a group consisting of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the disinfectant or antimicrobial agent comprises at least one of chlorhexidine gluconate and chlorhexidine diacetate.

In an embodiment, the disinfectant or antimicrobial agent is a fluid or a gel.

In a further exemplary embodiment of the present disclosure a method for disinfecting a female medical connector is disclosed. The method includes providing a rotatable inner housing that includes an absorbent material having a disinfectant or antimicrobial agent. The method also includes providing an outer housing that receives the inner housing wherein the inner housing and absorbent material are rotatable within the outer housing. The method further includes providing an indicator element having a first visual indicator and a second visual indicator concealed by the first visual indicator. A transparent collar is also provided wherein the collar includes at least one rib element that contacts the indicator element wherein rotation of the collar causes corresponding rotation of the absorbent material to disinfect the female connector. Rotation of the collar also causes the at least one rib element to remove sufficient portions of the indicator element to expose the second visual indicator to provide visual indication that the female connector is disinfected.

DETAILED DESCRIPTION

Figure 1:
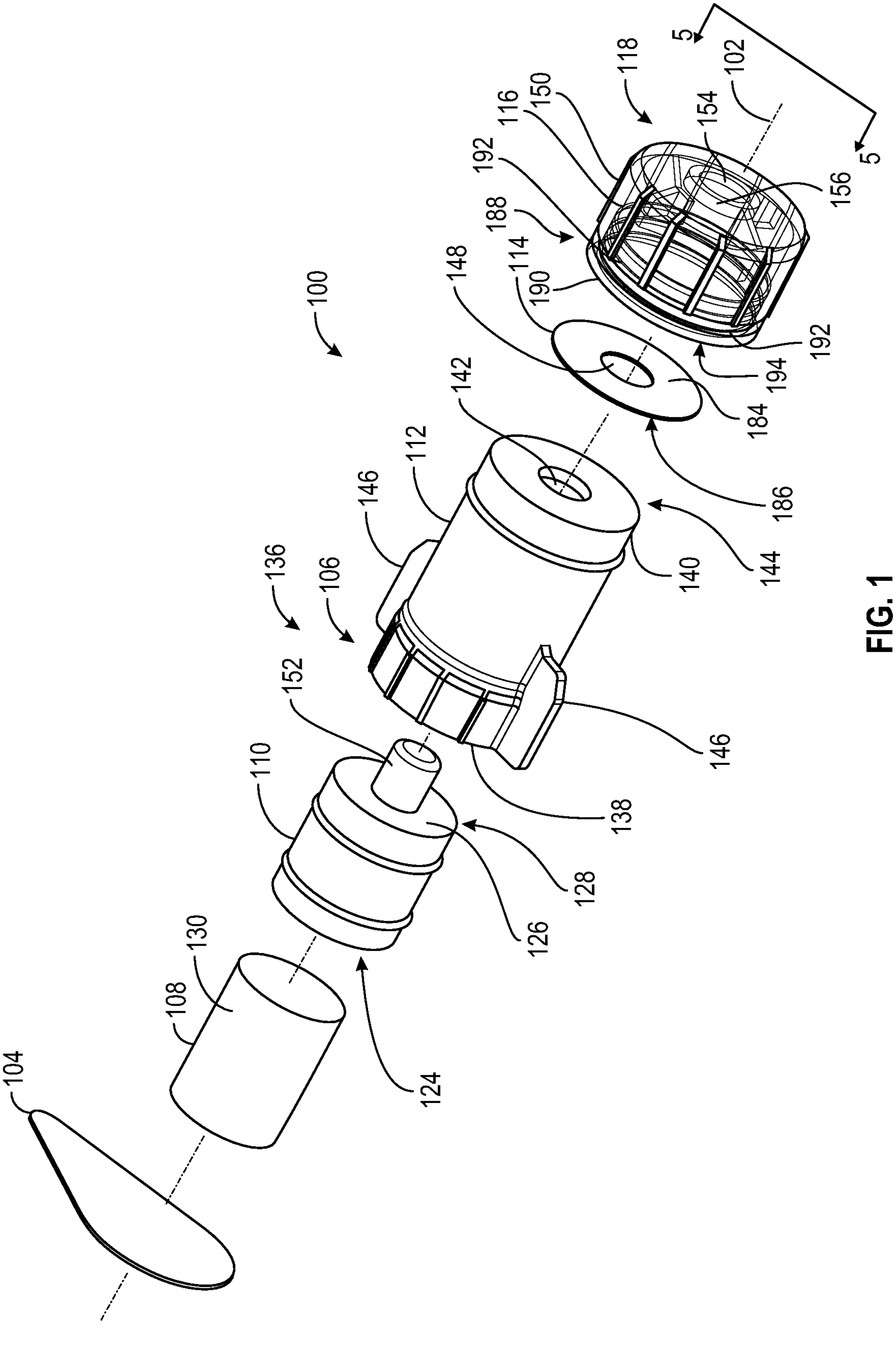
FIG. 1 is an exploded view of a disinfection device in accordance with the present disclosure.

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the disclosure pertain to a disinfection device for disinfecting a female medical connector such as female needleless connector. The device generally comprises an absorbent material having a disinfectant or antimicrobial agent, inner and outer housings, an indicator element, a transparent collar and a boss element. The inner housing includes an inner wall and a first open end that receives the absorbent material wherein the female connector is inserted into the first open end and contacts the absorbent material. The outer housing includes an outer wall and a second open end that receives the inner housing wherein the inner housing and absorbent material are rotatable within the outer housing. The indicator element is located between the outer wall and the transparent collar wherein the indicator element includes a first visual indicator and a second visual indicator concealed by the first visual indicator. In addition, the collar includes at least one rib element that contacts the indicator element. The boss element extends from the inner wall and through the outer wall and indicator element and is attached to the collar. Rotation of the collar causes corresponding rotation of the absorbent material to disinfect the female connector. Rotation of the collar also causes the at least one rib element to remove sufficient portions of the indicator element to expose the second visual indicator to provide visual indication that the female connector is disinfected.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a vascular access device (VAD). A Luer connector also has a distal end channel that releasably attaches the Luer connector to the hub of a VAD, and a proximal end channel that releasably attaches the Luer connector to the barrel of a syringe.

Figure 2:
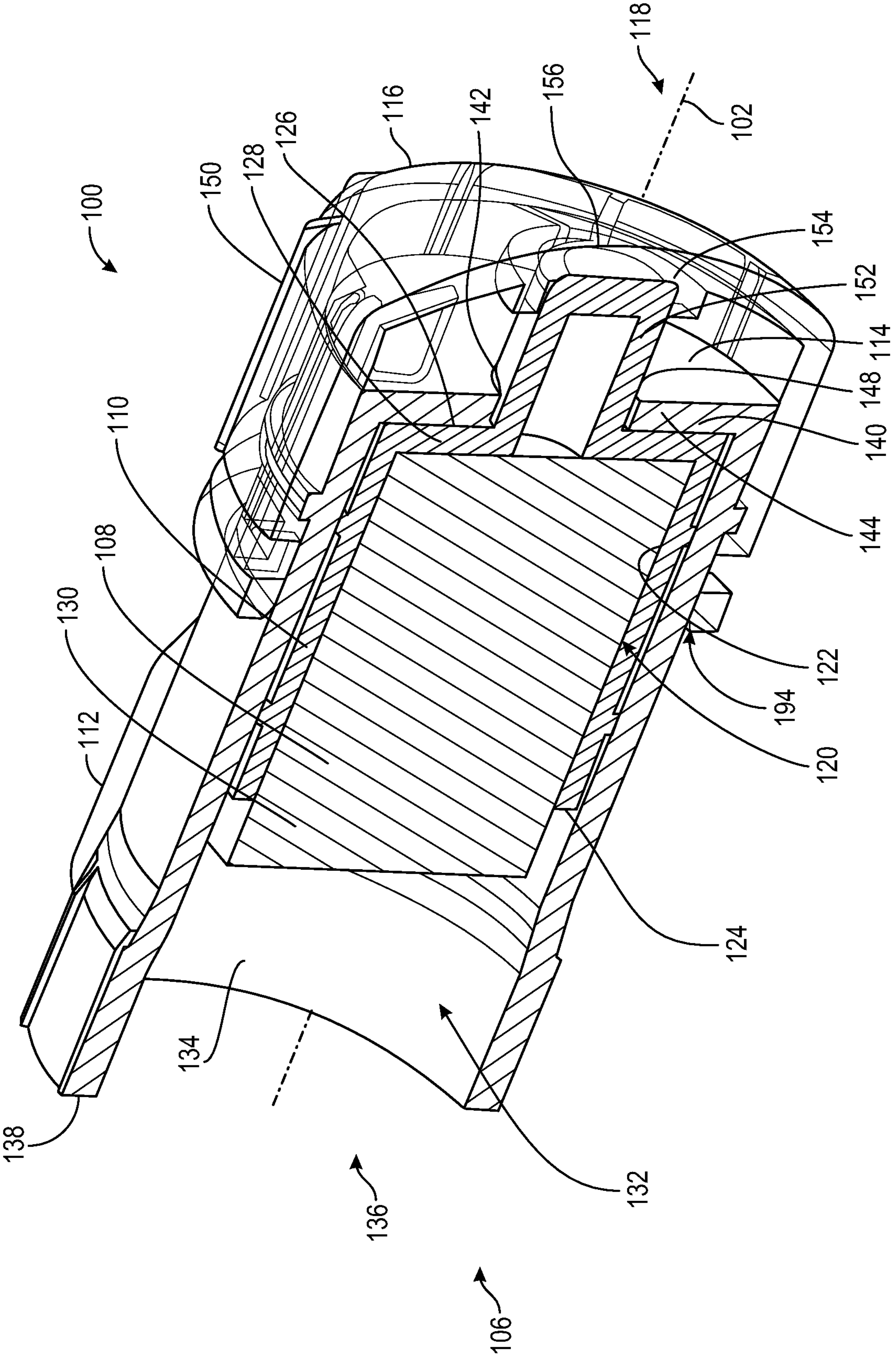
FIG. 2 is a cross sectional view of an assembled device.

Referring to FIG. 1, an exploded perspective view of a disinfection device 100 in accordance with the present disclosure is shown arranged relative to a center axis 102 of the device 100. FIG. 2 shows a cross sectional view of an assembled device 100. Referring to FIG. 1 in conjunction with FIG. 2, the device 100 includes a peelable seal 104 located at a first end 106 of the device 100, absorbent material 108, inner 110 and outer 112 housings having a substantially cylindrical shape, a stationary indicator element 114 and a rotatable collar element 116 having a substantially cylindrical shape located at a second end 118 of the device 100.

The inner housing 110 includes a first cavity 120 defined by a first interior wall 122 having a first diameter. The first cavity 120 extends through a first end of the inner housing 110 to form a first open end 124. The first open end 124 provides access to the absorbent material 108 as will be described. The inner housing 110 further includes an inner wall 126 located at a second end 128 opposite the first open end 124 that closes the first cavity 120.

The absorbent material 108 includes a disinfectant or an antimicrobial agent 130 for disinfecting a female connector. In one or more embodiments, the absorbent material 108 may be a nonwoven material, foam, or a sponge having a porous structure. In a specific embodiment, the foam is a polyurethane foam. In a specific embodiment, the absorbent material 108 is a sponge.

Absorbent material 108 retains disinfectant or antimicrobial agent 130 in its porous structure due to surface tension and releases disinfectant or antimicrobial agent 130 when squeezed or compressed by an incoming female connector. The device 100 is designed to be compatible in interacting with various disinfectants. In one or more embodiments, the disinfectant or antimicrobial agent 130 may include variations of alcohol or chlorhexidine. In one or more embodiments, the disinfectant or antimicrobial agent 130 is selected from the group consisting of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent 130 comprises at least one of chlorhexidine gluconate and chlorhexidine diacetate. In one or more embodiments, the disinfectant or antimicrobial agent 130 is a fluid or a gel. In one or more specific embodiments, the disinfectant or antimicrobial agent 130 is 70% isopropyl alcohol (IPA).

The outer housing 112 includes a second cavity 132 defined by a second interior wall 134 having a second diameter. The second cavity 132 extends through a first end of the outer housing 112 to form a second open end 136 having an annular engagement surface 138. The second cavity 132 is shaped and sized to receive the inner housing 110 and enable rotation of the inner housing 110 within the second cavity 132 about the center axis 102. The outer housing 112 further includes an outer wall 140 having an outer wall opening 142 that is aligned with the center axis 102. The outer wall 140 is located at a second end 144 opposite the second open end 136 and serves to close the second cavity 132. The outer housing 112 also includes a plurality of flange elements 146 that extend from the outer housing 112 to facilitate gripping or holding the outer housing 112 by a user such as a clinician, nurse or other health care provider.

The seal 104 is removably attached to the engagement surface 138 to seal the device 100. The seal 104 minimizes entry of potential particulate hazard and also provides a substantially impermeable enclosure for the device 100, provides a leak prevention and protection enclosure, protects the contents of absorbent material 130 contained within the first cavity 120, and/or maintains a sealed, sterilized environment. The seal 104 provides a sufficient seal at a range of temperatures, pressures, and humidity levels. In one or more embodiments, the seal 104 comprises an aluminum or multilayer polymer film peel back top. In a specific embodiment, the seal 104 is heat-sealed or induction sealed to the engagement surface 138.

The indicator element 114 is substantially ring shaped and includes an indicator element opening 148 that is aligned with the outer wall opening 142. The indicator element 114 is located between the outer wall 140 of the outer housing 112 and the collar 116 and may be attached to the outer wall 140 or formed unistructurally or integrally with the outer housing 112 to form a one piece structure. The collar 116 is substantially transparent to enable viewing of the indicator element 114 by a user. The collar 116 also includes a plurality of raised grip members 150 on an outside surface of the collar 116 to facilitate gripping the collar 116 by a user. In one or more embodiments, the collar 116 may include additional features, such as a textured surface, that also enhance gripping of the collar 116. The collar 116 further includes a collar wall 154 that defines a collar opening 156 that is aligned with the indicator element 148 and outer wall 142 openings along the center axis 102.

The inner wall 126 of the inner housing 110 further includes an extended boss element 152 that extends through the outer wall 142, indicator element 148 and collar 156 openings and is attached or bonded to the collar wall 154 with an adhesive or other attachment method. In one or more embodiments, the boss element 152 may be attached to other portions of the collar 116. In accordance with an aspect of the present disclosure, rotation of the collar 116 causes corresponding rotation of the inner housing 110 within the outer housing 112 about the center axis 102. Rotation of the inner housing 110 also rotates the absorbent material 108 which in turn disinfects a female connector as will be described. The outer housing 112 is stationary during rotation of the inner housing 110.

Figure 3:
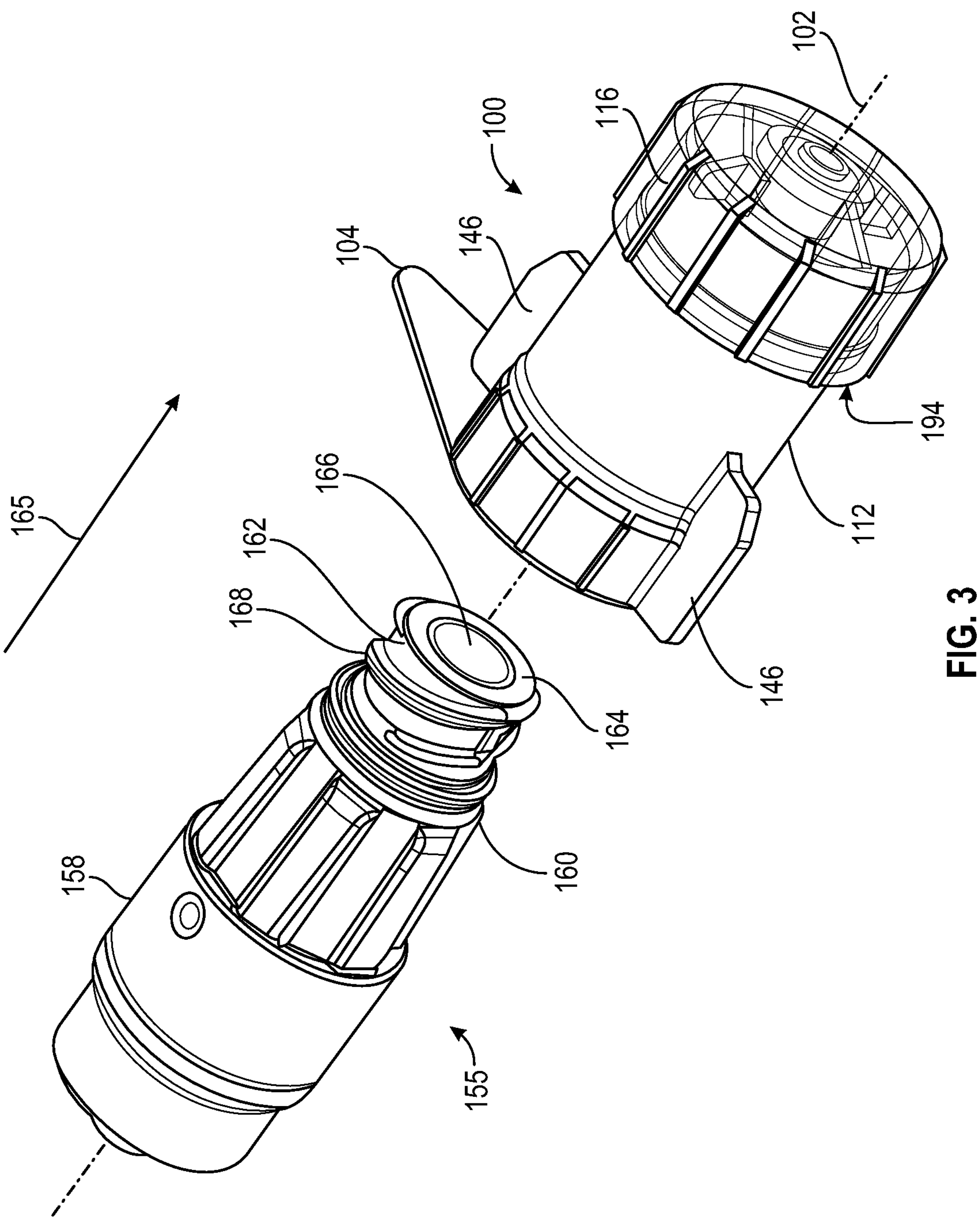
FIG. 3 is an assembled view of the device shown aligned with a female connector on a center axis.

Referring to FIG. 3, an assembled view of the device 100 is shown aligned with a female connector 155 on center axis 102. In one or more embodiments, the female connector 155 may be a needleless connector, catheter luer connector, stopcock, or hemodialysis connector. For purposes of illustration, the present disclosure will now be described when used in conjunction with a needleless connector 158. The connector 158 includes a hub portion 160 having a substantially cylindrically shaped outer hub surface 162 oriented substantially parallel to the center axis 102. The hub portion 160 further includes an access surface 164 that includes a septum 166. The access surface 164 and septum 166 are oriented substantially transverse to the hub surface 162. The hub surface 162 further includes hub threads 168 for threadably engaging the connector 158 with a known male connector of a syringe or other medical device or medical implement.

Figure 4:
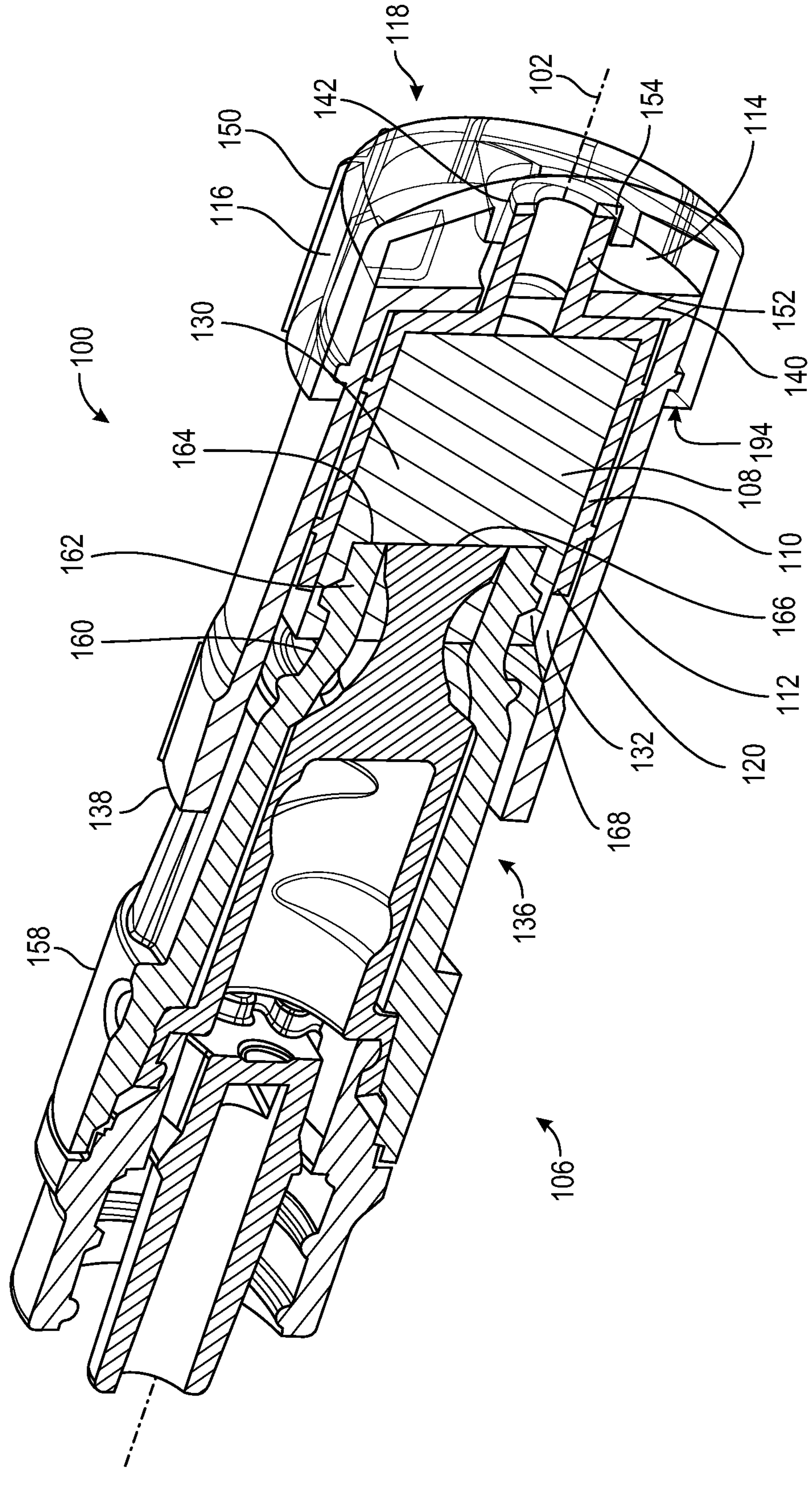
FIG. 4 is a cross sectional view of the device and female connector wherein a hub portion of the female connector is in an inserted position in the device.

In accordance with an aspect of the present disclosure, the hub portion 160 of the connector 158 is first inserted into the device 100 (see arrow 165) through the first open end 124 until the hub portion 160 contacts the absorbent material 108. FIG. 4 depicts a cross sectional view of the device 100 and connector 158 wherein the hub portion 160 is in an inserted position. In this position, the hub portion 160 is inserted into the absorbent material 108 such that the absorbent material 108 contacts the access surface 164 and septum 166 along with sides of the hub portion 160 including the hub surface 162 and hub threads 168. This compresses the absorbent material 108 and releases the disinfectant or antimicrobial agent 130 from the absorbent material 108 such that the disinfectant or antimicrobial agent 130 contacts the access surface 164, septum 166, hub surface 162 and hub threads 168 to provide passive disinfection of the access surface 164, septum 166, hub surface 162 and hub threads 168.

As previously described, rotation of the collar 116 causes corresponding rotation of the inner housing 110 and thus rotation of the absorbent material 108. In accordance with an aspect of the present disclosure, the collar 116 is rotated by a user when the hub portion 160 is in the inserted position. Rotation of the collar 116 frictionally engages the absorbent material 108 with the hub portion 160 to provide a scrubbing action on the access surface 164, septum 166, hub surface 162 and hub threads 168 that actively disinfects the access surface 164, septum 166, hub surface 162 and hub threads 168. In one or more embodiments, active disinfection due to rotation of the collar 116 is in addition to the passive disinfection of the hub portion 160 due to contact between the disinfectant or antimicrobial agent 130 and the access surface 164, septum 166, hub surface 162 and hub threads 168.

Figure 5:
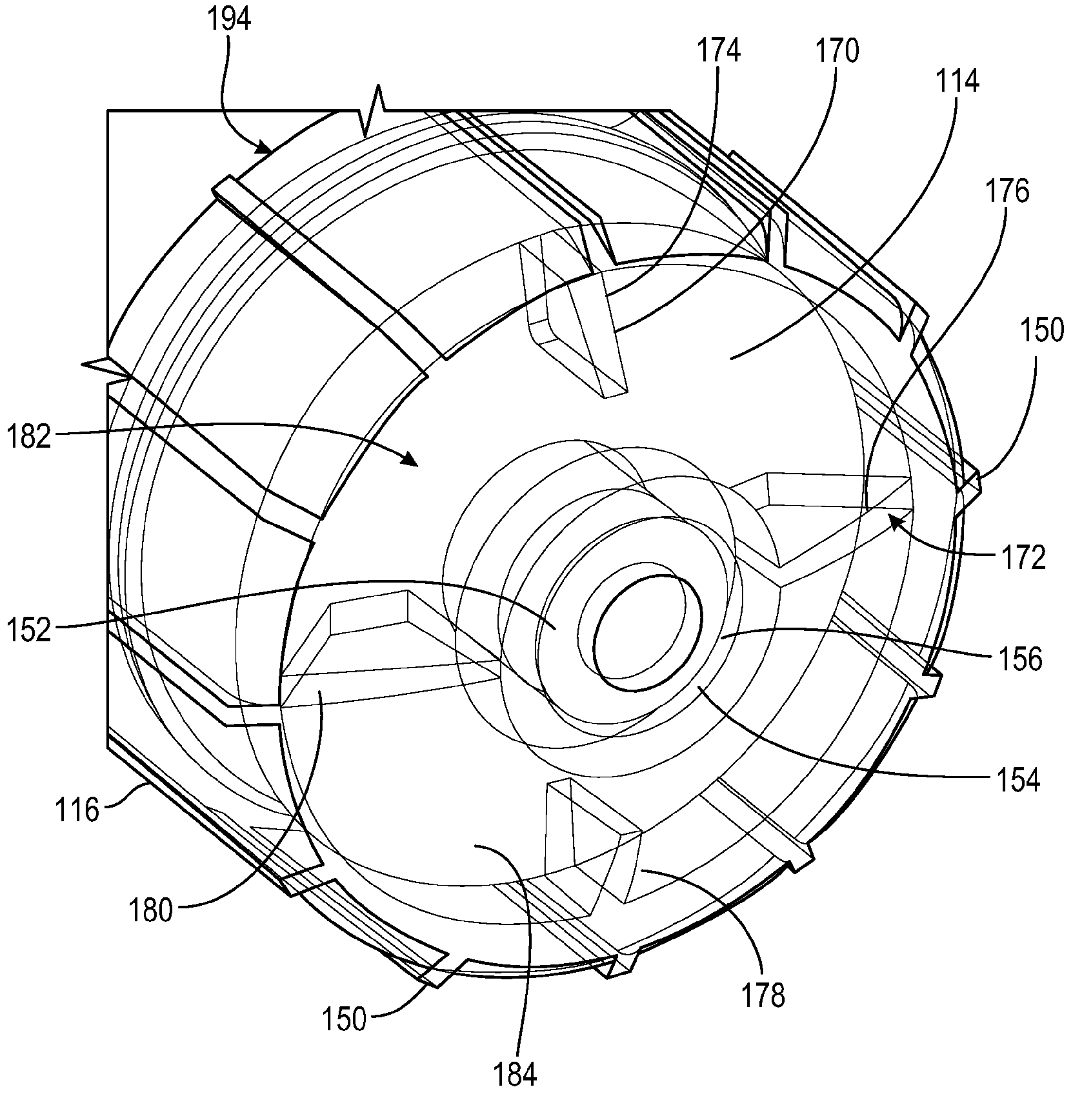
FIG. 5 is an enlarged view of a transparent collar along view line 5-5 of FIG. 1.

Referring to FIG. 5, an enlarged view of the transparent collar 116 along view line 5-5 of FIG. 1 is shown. The collar 116 includes at least one rib 170 that extends or projects from an interior surface 172 of the collar 116 and contact the indicator element 114. In an embodiment, the collar 116 includes first 174, second 176, third 178 and fourth 180 ribs that are equally spaced around an interior 182 of the collar 116.

The indicator element 114 includes a removable indicator top surface 184 that includes a first visual indicator that is visible through the transparent collar 116. The indicator surface 184 is manufactured using a known opaque coating material that cannot be seen through but can be scratched off. The indicator surface 184 is formed on a substrate 186 that includes a second visual indicator that is concealed by the indicator surface 184 and thus is not visible. In accordance with an aspect of the present disclosure, portions of the indicator surface 184 are removed when the collar 116 and thus first 174, second 176, third 178 and fourth 180 ribs are rotated against the indicator surface 184 due to contact between the first 174, second 176, third 178 and fourth 180 ribs and the indicator surface 184. For example, the first 174, second 176, third 178 and fourth 180 ribs may scratch, scrape or rub off the indicator surface 184 when the collar 116 is rotated. The collar 116 is rotated until a sufficient amount of the indicator surface 184 is removed such that the second visual indicator is fully exposed and becomes visible through the transparent collar 116. In accordance with an aspect of the present disclosure, the number of rotations of the collar 116 needed to fully expose the second visual indicator corresponds to an amount of scrubbing action needed to disinfect a portion of a female connector 155, such as the access surface 164, septum 166, hub surface 162 and hub threads 168 of connector 158. Thus, the device 100 provides passive visual indication to the user that the disinfection of the hub portion 160 is completed.

The indicator element 114 may be configured as a scratch card having a scratch card indicator surface 184 that is removed when the collar 116 is rotated and the first 174, second 176, third 178 and fourth 180 ribs scratch off the scratch card surface 184. In one or more embodiments, the indicator surface 184 may be fabricated using a known thin layer of opaque removable foil, ink, or other known opaque coating material that cannot be seen through but can be scratched off. Further, the first 174, second 176, third 178 and fourth 180 ribs may include an abrasive surface or raised edges to facilitate removal of the indicator surface 184. In an embodiment, the substrate 186 may be fabricated from a material having a suitable stiffness to enable removal of the indicator surface 184 by the first 174, second 176, third 178 and fourth 180 ribs.

Before the collar 116 is rotated, the first visual indicator of the indicator element 114 is visible through the transparent collar 116. As the collar 116 is rotated, portions of the indicator surface 184 and thus the first visual indicator are removed until only the second visual indicator formed on the substrate 186 is visible. In one or more embodiments, the first visual indicator may be a first color and the second visual indicator may be a second color. The indicator element 114 may be configured such that when the indicator surface 184 is completely removed, the indicator element 114 completely changes color to indicate that an amount of scrubbing action needed to disinfect a portion of a female connector 155, such as connector 158, has occurred. For example, a color of the indicator element 114 may change from black to white when viewed through the transparent collar 116 to indicate that connector 158 has been disinfected. Thus, the device 100 provides passive visual indication to the user that the disinfection of the hub portion 160 is completed. In one or more embodiments, the indicator element 114 may be configured to reveal indicia, graphics, symbols, diagrams, and/or words in addition to, or instead of, a change in color to indicate disinfection of a female connector.

Referring back to FIG. 1, the device 100 further includes a tamper evident structure 188 that indicates whether or not the collar 116 has already been rotated. In particular, the tamper evident structure 188 includes a ring member 190 that is stationary relative to the outer housing 112. In one or more embodiments, the ring member 190 may be attached to the outer housing 112 by an interference fit, an adhesive or formed unistructurally or integrally with the outer housing 112 to from a one piece structure. The tamper evident structure 188 also includes a plurality of breakable elements 192, such as breakable finger elements or thin rod elements, that are coupled between the collar 116 and ring member 90. The breakable elements 192 are configured to break when the collar 116 is rotated by hand with sufficient torque, thus separating the collar 116 from the ring member 188 to enable rotation of the collar 116 by a user. The tamper evident structure 188 indicates if the collar 116 has already been rotated. In particular, the tamper evident structure 188 would indicate to a user that the device 100 may have already been used for disinfection if the breakable elements 192 are already broken. The tamper evident structure 188 also inhibits accidental rotation of the collar 116.

The device can be made from any of a number of types of plastic materials such as polycarbonate, polypropylene, polyethylene, glycol-modified polyethylene terephthalate, acrylonitrile butadiene styrene or any other moldable plastic material used in medical devices. In one or more embodiments, the device comprises a polypropylene or polyethylene material.

Figure 6A:
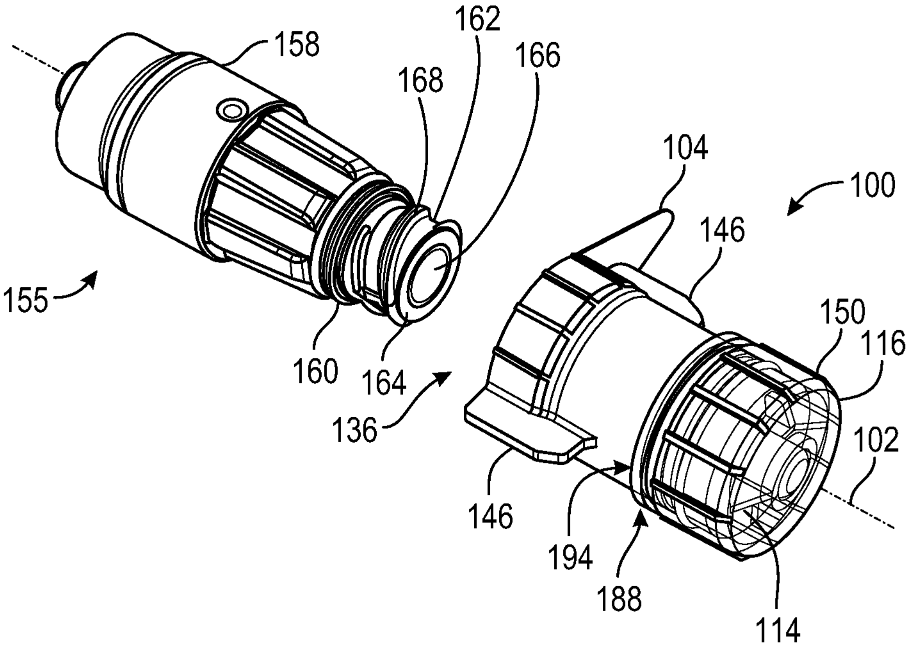
FIGS. 6A-6D depict exemplary operation of the device.
Figure 6B:
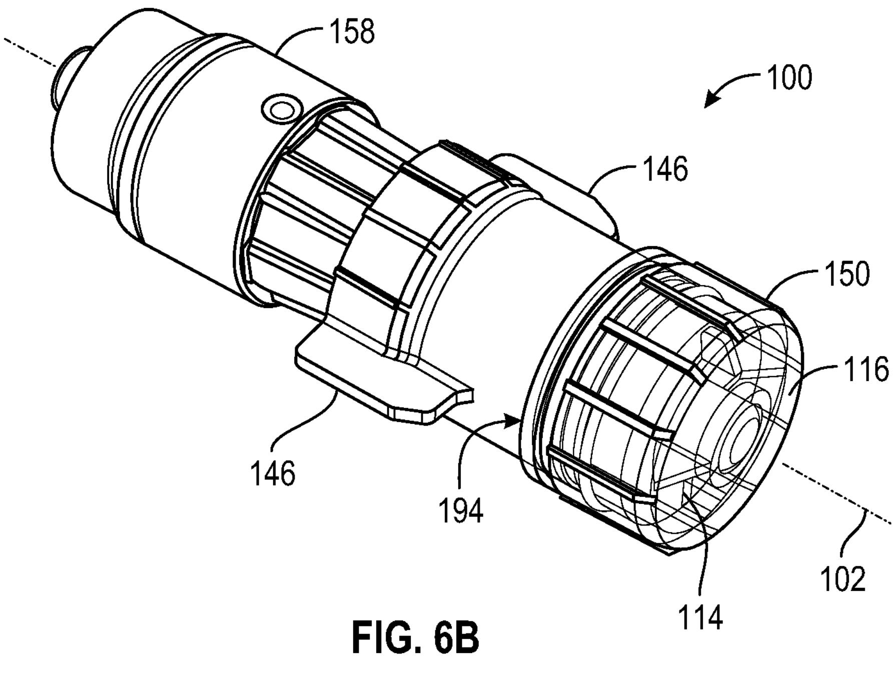

Exemplary operation of the device 100 to disinfect a female connector will now be described in conjunction with FIGS. 6A-6D. For purposes of illustration, operation of the device 100 will be described in conjunction with the connector 158 although the device 100 is also applicable to another type of female connector 155 such as catheter luer connector, stopcock, or hemodialysis connector. Referring to FIG. 6A, the seal 104 is removed to provide access to the absorbent material 108 for the connector 158 (see also FIG. 1) and the device 100 is substantially aligned with connector 158 on center axis 102. Referring to FIG. 6B, the hub portion 160 of the connector 158 is inserted into the device 100 through the first open end 124 until the hub portion 160 contacts the absorbent material 108 in an inserted position. In this position, the hub portion 160 is inserted into the absorbent material 108 such that the absorbent material 108 contacts the access surface 164 and septum 166 along with sides of the hub portion 160 including the hub surface 162 and hub threads 168. This compresses the absorbent material 108 and releases the disinfectant or antimicrobial agent 130 from the absorbent material 108 such that the disinfectant or antimicrobial agent 130 contacts the access surface 164, septum 166, hub surface 162 and hub threads 168 to provide passive disinfection of the access surface 164, septum 166, hub surface 162 and hub threads 168 (see also FIG. 4).

Figure 6C:
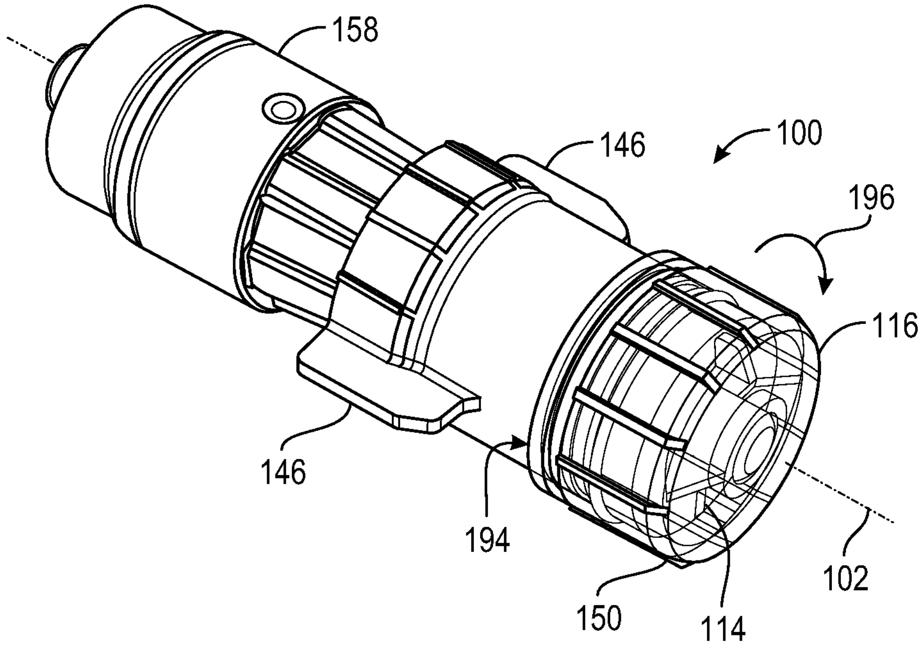

Referring to FIG. 6C, a user then grasps the connector 158 and flange elements 146 with one hand and begins to rotate the collar 116 in a first direction, such as a clockwise direction (sec arrow 196), about the center axis 102 with the other hand. When this occurs, the breakable elements 192 (see FIG. 1) of the tamper evident structure 188 break to allow rotation of the collar 116. During rotation of the collar 116, portions of the indicator surface 184 are removed when the collar 116 and thus first 174, second 176, third 178 and fourth 180 ribs are rotated against the indicator surface 184 due to contact between the first 174, second 176, third 178 and fourth 180 ribs and the indicator surface 184. Rotation of the collar 16 also frictionally engages the absorbent material 108 with the hub portion 160 to provide a scrubbing action on the access surface 164, septum 166, hub surface 162 and hub threads 168 that actively disinfects the access surface 164, septum 166, hub surface 162 and hub threads 168.

Figure 6D:
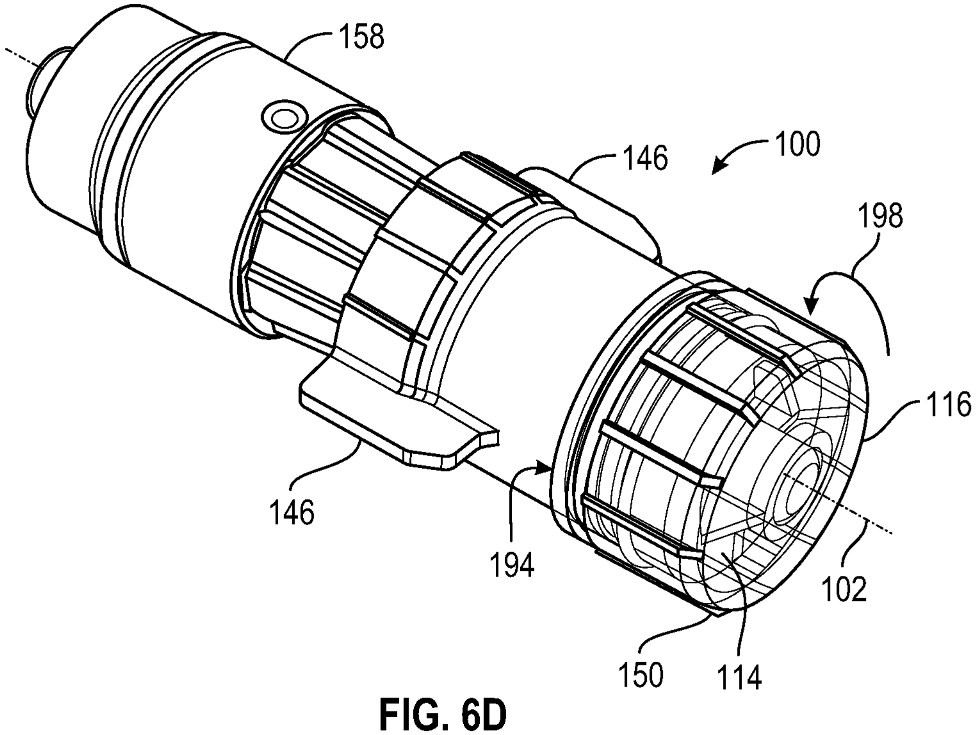

Referring to FIG. 6D, the collar 116 may then be rotated in an opposite direction, such as a counterclockwise direction (see arrow 198). The collar 116 is rotated until a sufficient amount of the indicator surface 184 is removed such that the second visual indicator is fully exposed and becomes visible through the transparent collar 116. In accordance with an aspect of the present disclosure, the number of rotations of the collar 116 needed to fully expose the second visual indicator corresponds to an amount of scrubbing action needed to disinfect a portion of a female connector 155, such as the access surface 164, septum 166, hub surface 162 and hub threads 168 of connector 158.

For example, a color of the indicator element 114 may change from black to white when viewed through the transparent collar 116 to indicate that connector 158 has been disinfected. Therefore, the device 100 provides passive visual indication to the user that the disinfection of the hub portion 160 is completed. In one or more embodiments, the indicator element 114 may be configured to reveal indicia, graphics, symbols, diagrams, and/or words in addition to, or instead of, a change in color to indicate disinfection of a female connector. Thus, the combination of passive disinfection with active disinfection results in improved disinfection results.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection device for disinfecting a female medical connector, the disinfection device comprising:

an absorbent material having a disinfectant or antimicrobial agent;

an inner housing having an inner wall and a first open end that receives the absorbent material wherein the female connector is inserted into the first open end and contacts the absorbent material;

an outer housing having an outer wall and a second open end that receives the inner housing wherein the inner housing and absorbent material are rotatable within the outer housing;

an indicator element located between the outer wall and a transparent collar having at least one rib element that contacts the indicator element wherein the indicator element includes a first visual indicator and a second visual indicator concealed by the first visual indicator; and a boss element that extends from the inner wall and through the outer wall and indicator element and is attached to the collar, wherein rotation of the collar causes corresponding rotation of the absorbent material to disinfect the female connector wherein rotation of the collar also causes the at least one rib element to remove sufficient portions of the indicator element to expose the second visual indicator to provide visual indication that the female connector is disinfected.

2. The disinfection device of claim 1, wherein the female medical connector is selected from a group consisting of needleless connectors, catheter luer connectors, stopcocks, or hemodialysis connectors.

3. The disinfection device of claim 1, wherein the female medical connector is a needleless connector having an access surface, septum, hub surface and hub threads.

4. The disinfection device of claim 1, wherein the indicator element is a scratch card having a removable scratch card surface.

5. The disinfection device of claim 1, wherein the indicator element includes an indicator surface fabricated using a layer of removable foil.

6. The disinfection device of claim 1, wherein the first visual indicator is a first color and the second visual indicator is a second color.

7. The disinfection device of claim 1, further including a plurality of flanges that extend from the outer housing to facilitate handling of the outer housing by a user.

8. The disinfection device of claim 1, wherein the collar includes a plurality of raised grip members to facilitate gripping the collar by a user.

9. A disinfection device for disinfecting a female medical connector, the disinfection device comprising:

an absorbent material having a disinfectant or antimicrobial agent;

an inner housing having an inner wall and a first open end that receives the absorbent material wherein the female connector is inserted into the first open end and contacts the absorbent material;

an outer housing having an outer wall and a second open end that receives the inner housing wherein the inner housing and absorbent material are rotatable within the outer housing wherein a plurality of flanges extend from the outer housing to facilitate handling of the outer housing by a user;

an indicator element located between the outer wall and a transparent collar having at least one rib element that contacts the indicator element wherein the indicator element includes a first visual indicator and a second visual indicator concealed by the first visual indicator;

a boss element that extends from the inner wall and through the outer wall and indicator element and is attached to the collar, wherein rotation of the collar causes corresponding rotation of the absorbent material to disinfect the female connector wherein rotation of the collar also causes the at least one rib element to remove sufficient portions of the indicator element to expose the second visual indicator to provide visual indication that the female connector is disinfected; and a ring member attached to the outer housing and coupled to the collar by a plurality of breakable elements to form a tamper evident structure wherein the breakable elements are configured to break when the collar is rotated with sufficient torque wherein broken finger elements indicate that the collar has been rotated.

10. The disinfection device of claim 9, wherein the female medical connector is selected from a group consisting essentially of needleless connectors, catheter luer connectors, stopcocks, or hemodialysis connectors.

11. The disinfection device of claim 9, wherein the female medical connector is a needleless connector having an access surface, septum, hub surface and hub threads.

12. The disinfection device of claim 9, wherein the indicator element is a scratch card having a removable scratch card surface.

13. The disinfection device of claim 9, wherein the indicator element includes an indicator surface fabricated using a layer of removable foil.

14. The disinfection device of claim 9, wherein the collar includes a plurality of raised grip members to facilitate gripping the collar by a user.

15. The disinfection device of claim 9, wherein the first visual indicator is a first color and the second visual indicator is a second color.

16. The disinfection device of claim 9, wherein the second open end forms an annular engagement surface and the disinfection device further includes a peelable seal removably attached to the annular engagement surface to prevent the disinfectant or the antimicrobial agent from exiting the disinfection device.

17. The disinfection device of claim 9, wherein the disinfectant or antimicrobial agent is selected from a group consisting essentially of isopropyl alcohol, ethanol, 2-propanol, butanol, methylparaben, ethylparaben, propylparaben, propyl gallate, hydroxyanisole butylated (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

18. The disinfection device of claim 17, wherein the disinfectant or antimicrobial agent comprises at least one of chlorhexidine gluconate and chlorhexidine diacetate.

19. The disinfection device of claim 18, wherein the disinfectant or antimicrobial agent is a fluid or a gel.

20. A method for disinfecting a female medical connector, the method comprising:

providing a rotatable inner housing that includes an absorbent material having a disinfectant or antimicrobial agent;

providing an outer housing that receives the inner housing wherein the inner housing and absorbent material are rotatable within the outer housing;

providing an indicator element having a first visual indicator and a second visual indicator concealed by the first visual indicator;

providing a transparent collar having at least one rib element that contacts the indicator element;

performing rotation of the collar wherein rotation of the collar causes corresponding rotation of the absorbent material to disinfect the female connector wherein rotation of the collar also causes the at least one rib element to remove sufficient portions of the indicator element to expose the second visual indicator to provide visual indication that the female connector is disinfected.

* * * * *